United States Patent [19]

Brock

[11] 4,220,660
[45] Sep. 2, 1980

[54] PROCESS FOR THE TREATMENT OF HUMANS SUFFERING FROM UNDESIRED UROTOXIC SIDE EFFECTS CAUSED BY CYTOSTATICALLY ACTIVE ALKYLATING AGENTS

[75] Inventor: Norbert Brock, Bielefeld, Fed. Rep. of Germany

[73] Assignee: Asta-Werke Aktiengesellschaft, Chemische Fabrik, Bielefeld, Fed. Rep. of Germany

[21] Appl. No.: 967,000

[22] Filed: Dec. 6, 1978

[30] Foreign Application Priority Data

Dec. 14, 1977 [DE] Fed. Rep. of Germany ....... 2756018
Jun. 23, 1978 [DE] Fed. Rep. of Germany ....... 2827625

[51] Int. Cl.² .................................... A61K 31/185
[52] U.S. Cl. ........................................ 424/315
[58] Field of Search ........................... 424/315

[56] References Cited

PUBLICATIONS

Chemical Abstracts 55:12660f (1961).

Primary Examiner—Jerome D. Goldberg
Attorney, Agent, or Firm—Schwartz, Jeffery, Schwaab, Mack, Blumenthal & Koch

[57] ABSTRACT

The invention is related to a process for the treatment of humans suffering from undesired urotoxic side effects caused by cytostatically active alkylating agents administered to them against malign tumors, comprising administering a pharmacologically acceptable salt of a mercapto alkane sulfonic acid having the general formula

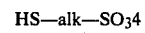

$$HS-alk-SO_34$$

to the human treated with the cytostatically active alkylating agent, in an amount ranging from 20% of the weight of the alkylating agent to the highest tolerated dosage of the salt of the mercapto alkane sulfonic acid, simultaneously or separately in combination with the alkylating agent.

7 Claims, No Drawings

PROCESS FOR THE TREATMENT OF HUMANS SUFFERING FROM UNDESIRED UROTOXIC SIDE EFFECTS CAUSED BY CYTOSTATICALLY ACTIVE ALKYLATING AGENTS

The present invention is directed to a new use of salts of mercapto alkane sulfonic acids in the cytostatic therapy with alkylating agents. More in particular, the present invention is related to a process for the treatment of humans who are treated with alkylating agents against malign tumors and who suffer from the undesired urotoxic side effects caused by such alkylating agents in the kidneys, urinary tracts and urinary bladder.

Cytostatically active alkylating agents such as melphalane, cyclophosphamide, trofosfamide, ifosfamide, sufosfamide, chlorambucil, busulfane, triethylene thiophosphamide or triaziquone and in particular the 2-oxo-1,3,2-oxazaphosphorinanes cyclophosphamide, trofosfamide, ifosfamide and sufosfamide produce undesired side effects such as serious irritations of the kidneys, the urinary tracts and/or the urinary bladder of the patient treated therewith. As is well known, such undesired side effects occur readily in particular after such organs have been damaged for the first time. The undesired side effects are sometimes produced to such a degree that the cytostatic therapy of the patient suffering from cancer has to be interrupted temporarily or is rendered even impossible at all. In view of the fact that malign tumors readily produce resistency against a particular cytostatic, such cytostatics are successfull in the so-called high dosage therapy. In such a treatment, the cytostatic is administered at first in a dosage which is very high in comparison to the toxicity of the cytostatic in order to produce an initial dosage as high as possible of the cytostatic at the tumor tissue. Thereafter, the cytostatics are administered in several lower dosages over a prolonged period of time. It is known that such undesired side effects are caused by metabolites of the cytostatics produced in the body of the patient treated therewith. These undesired side effects quite often occur also with alkylating agents such as 2-[N,N-bis(2-chloroethyl)-amino]-2-oxo-1,3,2-oxazaphosphorinane known under the well-known trade names Endoxan ® or Cytoxan ® or under the generic name cyclophosphamide, and 2-[N,N-bis(2-chloroethyl)-amino]-3-(2-chloroethyl)-2-oxo-1,3,2-oxazaphosphorinane known under the trade name Ixoten ® or the generic name trofosfamide. Of even more importance are these undesired side effects when using alkylating agents having a high cytostatic activity at a lower toxicity such as 2-(N-2-chloroethyl-amino)-3-(2-chloroethyl)-2-oxo-1,3,2-oxazaphosphorinane known under the generic name ifosfamide. The therapeutic usefulness of such valuable alkylating agents which is particularly based upon the low toxicity, is again substantially limited by these undesired side effects. It has been observed recently that such irritations of the urinary bladder may even cause the formation of malign tumors there.

Many experiments have been made in order to avoid or at least alleviate these detrimental and undesired side effects of the cytostatically active alkylating agents since they can no more be replaced in the treatment of malign tumors, and a premature rupture of the therapy would produce severe damage or premature death of the patient. One of the attempts consists in the administration of increased amounts of liquid, possibly in combination with the administration of agents increasing the formation of urine in order to obtain a passage of urine containing metabolites of cytostatics as quick as possible through the kidneys, the urinary tracts and the urinary bladder and to avoid the formation of high concentrations of metabolites in particular in the urinary bladder. This so-called hydratation in general is combined with an alkalinization of the urine for instance by means of the hexapotassium hexasodium pentacitrate hydrate complex known under the registered trade name Uralyt-U and in particular by introducing solutions of mercapto group containing compounds into the urinary bladder by means of a catheter. With such mercapto group containing compounds it was supposed that the mercapto group undergoes reaction with the alkylating agent, thus inactivating the same. N-Acetyl cysteine and cysteine in particular have been used as such mercapto group containing compounds. However, the results only where very limited, in particular in cases where the cytostatics had to be administered in very high dosages. Furthermore, the washing of the urinary bladder or vesicocylsis is a procedure very burdensome to the patient, and can only very hardly be practiced in the treatment with cytostatics over prolonged periods of time. Furthermore, more upward areas in the urinary tract cannot be reached by vesicoclysis.

The use of mercapto group containing compounds for the general detoxification in the therapy with alkylating agents has been first published by T. A. Connors, Europ. J. Cancer 2, 393 to 395 (1966). However, these experiments showed no result because the mercapto group containing compounds there used at the same time decreased the cytostatic activity of the alkylating agents (see in particular loc. cit., p. 300 and 303, last but one sentence).

After introduction of the 2-oxo-1,3,2-oxazaphosphorinanes as alkylating agents and after observation of urotoxic side effects (hemorrhaginal cysto-pyelonephritis), the first attempts to avoid such undesired side effects where made by topically applying mercapto group containing compounds in the urinary bladder itself. This instillation of N-acetylcysteine up to now represented a standard prophylaxis against urotoxic side effects when administering cyclofosfamide and ifosfamide at very high dosages (see for instance Hoefer-Janker et al., Med. Welt 26, 972 (1975); Drings et al., Verh. Dtsch. Ges. inn. Med. 78, 166 (1972); Cohen et al., Cancer Chemother. Rep., Part 1, 59, 751 (1975); Creaven et al., Cancer Treatm. Rep. 60, 445 (1976); and Primack, J. Nat. Cancer Inst. 47, 223 (1971)).

However, the instillation of HS-group containing compounds into the urinary bladder did not solve the problem of a general detoxification. The beneficial effects of the applied mercapto group containing compound were limited to the urinary bladder. Furthermore, the application by means of a catheter was not regarded as most favorable. Finally, the clinical effectiveness of this burdensome prophylaxis by no means was satisfactory (see for instance Falkson, Suid-Afrikaanse Kankerbulletin 15, 97, 1971).

It is an object of the present invention to provide improved means to avoid the undesired urotoxic activity of alkylating agents when used in the treatment of cancer in humans.

It surprisingly now has been found that the above described undesired urotoxic side effect produced by cytostatically active alkylating agents in the kidney, the urinary tract and the urinary bladder of patients treated therewith may be overcome in a simple manner and to a substantially complete degree by administering in combination with the alkylating agent a known pharmacologically acceptable salt of a mercapto alkane sulfonic acid having the general formula

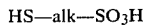

wherein alk is a straight or branched alkylene group having from 2 to 6, in particular from 2 to 4 carbon atoms. The present invention therefore is directed to the use of such pharmacologically acceptable salts of mercapto alkane sulfonic acids in the cytostatic therapy with alkylating agents, or, with other words, to a process for the treatment of humans who are treated with cytostatically active alkylating agents against malign tumors and who suffer from the undesired urotoxic side effects caused by such alkylating agents in the kidneys, the urinary tracts and the urinary bladder. This process comprises administering such a pharmacologically acceptable salt of a mercapto alkane sulfonic acid during a period of from about 30 minutes before administration of the alkylating agent until about 30 minutes after its administration and in an amount ranging from at least 20% of the amount of the alkylating agent administered or to be administered to the patient up to the highest dose of the salt of the mercapto alkane sulfonic acid which is tolerated by the patient. The salt of the mercapto alkane sulfonic acid may be administered together with the alkylating agent in a single dosage form, for instance in a capsule containing both agents, or in the same dosage form as the cytostatic, for instance both agents in capsules separately. Or they may be administered in separate usual dosage forms. For instance, the cytostatic may be administered intravenously while the salt of the mercapto alkane sulfonic acid is administered perorally or intraperitoneally. The detoxification of the alkylating agents and its metabolites according to the process of the present invention may be effected also by administering only 25% of the above defined or any hereinafter given preferred total dose within the above defined time relation to the administration of the alkylating agents and by administering the remainder of this total dose in one or several partial doses spread over a period of up to 12 hours after the administration of the alkylating agent. It has been found that it is only necessary to administer the salt of the mercapto alkane sulfonic acid such that there is present a certain minimum amount of the salt of the mercapto alkane sulfonic acid in the kidney and urinary bladder in order to effect detoxification of the separated and there present cytostatic or metabolite thereof and thereby effectively avoid the undesired urotoxic side effect to the kidney, the urinary tracts and the urinary bladder.

Preferably, the salt of the mercapto alkane sulfonic acid is simultaneously administered with the cytostatically active alkylating agent. This is particularly desirable with the high initial dose usual in the massive-dose therapy. At this occasion it is preferred that both active agents are administered in a single dosage unit.

Thus, the present invention is related to the use of a pharmacologically acceptable salt of a mercapto alkane sulfonic acid having the general formula

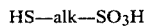

wherein alk is a straight or branched alkylene group having from 2 to 6 carbon atoms in the cytostatic therapy of humans with alkylating agents, either in the form of a combination product containing both the salt and the alkylating agent or in the form of separate dosage forms to be used simultaneously or separately in certain intervals.

Particularly good detoxification results have been obtained with such salts of 2-mercapto ethane sulfonic acid. Thus, the use of pharmacologically acceptable salts of 2-mercapto ethane sulfonic acid are preferred in the cytostatic therapy with alkylating agents according to the present invention. Particularly preferred among these salts are the alkali metal salts of 2-mercapto ethane sulfonic acid, in particular its sodium salt. This is the most preferably used salt.

In order to obtain an effective protection of the patient treated with cytostatically active alkylating agents against the urotoxic side effects upon the kidney, the urinary tracts and the urinary bladder it is sufficient to use so small amounts such as 20% of the amount of cytostatic administered. This is particularly true at low doses of the cytostatic. If the alkylating agent is administered in higher doses, the urotoxic side effect may be avoided with 30% of the amount of the alkylating agent administered. Since the urotoxic side effects in particular occur upon administration of the cytostatic at high doses, the lower limit of 30% of the amount of cytostatic administered is the preferred lower limit for the amount of the salt of the mercapto alkane sulfonic acid administered for detoxification of the cytostatics and their metabolites in the kidney, urinary tracts and urinary bladder. In view of the known very low toxicity of the pharmacologically acceptable salts of the mercapto alkane sulfonic acids, the upper limit of the amount of salts of mercapto alkane sulfonic acids is of minor importance. It is surprising and important that the cytostatic activity of the alkylating agents is not at all decreased or otherwise affected by the use of the salts of mercapto alkane sulfonic acids in accordance with the present invention. Even when administering the sodium salt of 2-mercapto ethane sulfonic acid in a dose amounting to 100 times the dose of ifosfamide there was observed now such decrease in cytostatic activity in test animals. Since the undesired urotoxic side effects even at high doses of the cytostatic may be substantially completely removed with equal amounts of the salts of the mercapto alkane sulfonics acids, it is preferred to use the salt of the mercapto alkane sulfonic acids in amounts corresponding to 30 to 100% of the amount of cytostatic to be administered or, respectively, already administered to the patient.

While the salts of the mercapto alkane sulfonic acids may be used in combination with all of the cytostatically active alkylating agents to overcome the above described urotoxic and in particular undesired side effects, these salts of mercapto alkane sulfonic acids are of particular importance in combination with the 2-oxo-1,3,2-oxazaphosphorinanes cyclophosphamide, ifosfamide, trofosfamide and sufosfamide used to a great extent in the treatment of humans suffering from many kinds of cancer diseases.

The pharmacologically acceptable salts of mercapto alkane sulfonic acids used in accordance to the present invention are known compounds (see U.S. Pat. No. 2,694,732). They have been used already for therapeutical purposes, namely as mucolytically active compounds and in dosage forms different from those as they are necessary in the use according to the present invention (see German Offenlegungsschrift No. 1,620,629). These or similar compounds up to now have however never been used to treat patients suffering from the described urotoxic side effects of cytostatically active alkylating agents. Up to now the medical profession was of the opinion that the alkylating agents or, respectively, metabolites thereof causing these undesired side effects have to be detoxified topically at the place where they produce the injury and damage and that mercapto group containing compounds have to be applied in these damaged areas (for instance by installation into the urinary bladder of the cytostatically treated patient) so that they produce their beneficial detoxifying activity at the place of damage. Furthermore, the mercapto group containing compounds used up to now showed to be ineffective with this respect when applied orally. Still furthermore, it was the opinion of the medical profession that the cytostatic activity of the alkylating agents is produced just by the metabolites blamed for the urotoxic side effects and that, therefore, the mercapto group containing compounds have to be administered as late as possible in the passage through the human body in order to avoid a negative influence upon the cytostatic activity of the alkylating agents and their metabolites. However, even with the mercapto group containing compounds used up to now the degree of detoxification only was quite limited. The undesired side effects described hereinabove can be overcome only to a very limited degree. Thus, it is not only surprising that the salts of mercapto alkane sulfonic acids proposed for use in accordance with the present application allow to completely avoid these undesired side effects when applied shortly before the administration of the alkylating agent or simultaneously therewith or shortly thereafter, but it is even more surprising that these salts produce this complete detoxification upon oral administration and upon administration spread over a prolonged period of time after administering the alkylating agent.

The following examples serve to further illustrate the present invention without however limiting the same thereto.

EXAMPLES

1. In accordance with the known practice of therapy, a patient 56 years old and suffering from a hypernephroma of the kidney at first is subjected to irradiation and thereafter is treated with ifosfamide [i.e. 2-(N-2-chloroethylamino)-3-(2-chloroethyl)-2-oxo-1,3,2-oxazaphosphorinane] at 5 times per day, each time with 60 mg./kg. intravenously and and at 5 subsequent days. The patient is simultaneously hydrated by administration of 4 liters of water spread over the day and is alkalinized by administration of hexapotassium hexasodium pentacitrate hydrate complex. The patient showed macrohematuria already on the third day after treatment. This caused immidiate rupture of the therapy. After a recovery period of 14 days the therapy is repeated. However, 35 mg./kg. of the sodium salt of 2-mercapto ethane sulfonic acid is administered intravenously and simultaneously with each dose of 60 mg./kg. of ifosfamide. The patient is controlled daily for micro- and macrohematuria and for albuminuria. There was found no indication of hematuria or albuminuria.

2. In another patient suffering from the same kind of cancer, therapy was effected immediately with simultaneous administration of equal doses of the sodium salt of 2-mercapto ethane sulfonic acid. There was observed no indication of hematuria.

3. Of two further patients in an analogous situation of cancer, one was treated with 21.5 mg./kg. of the sodium salt of 2-mercapto ethane sulfonic acid per each 60 mg./kg. dose of the alkylating agent while the other was treated with 60 mg./kg. of the sodium salt of 2-mercapto ethane sulfonic acid per each 60 mg./kg. of the alkylating agent with the same favorable results.

4. In several similar cases the sodium salt of 2-mercapto ethane sulfonic acid was administered orally ½ hour before the administration of the alkylating agent. At a dose between 30 and 60 mg./kg. of the sodium salt of 2-mercapto ethane sulfonic acid and a dose of 60 mg./kg. of the alkylating agent the complete detoxification and avoidance of the undesired side effect was observed.

Production of Combination Products

5. One part by weight of ifosfamide and 0.63 parts by weight of the sodium salt of 2-mercapto ethane sulfonic acid, both in pure sterile form, are homogenously mixed under sterile conditions in a sterile mixer and filled into injection ampoules such that each ampoule contains 500 mg. of ifosfamide and 315 mg. of the sodium salt of 2-mercapto ethane sulfonic acid per 10 ml. of injection solution.

6. Example 5 is repeated substituting ifosfamide by the same amount of cyclophosphamide, trofosfamide or sufosfamide.

The surprising effectiveness of the use of salts of various mercapto alkane sulfonic acids in accordance with the present invention is shown hereinafter with two different alkylating agents in test animals generally used and accepted by the researchers in this field to allow a conclusion for analogous results in humans.

The effectiveness of the salts of mercapto alkane sulfonic acids of the general formula $HS-alk-SO_3H$ is shown on the model of cystitis in rats caused by alkylating agents. The cystitis in rats is caused by single intravenous administration of 68.1 mg./kg. of ifosfamide or cyclophosphamide. 24 hours after administration of the alkylating agent a solution of Trypan blue is administered intravenously and the animals are killed in ether narcosis 30 minutes thereafter. The places of inflammation in the urinary bladder of the test animals is readily seen macroscopically by the vital staining with Trypan blue. The urinary bladder of the test animals are stained deeply blue and were heavily swollen and partly showed hemorrhage.

The salts of mercapto alkane sulfonic acids used in accordance with the present invention and tested in the present tests were administered intravenously to the test animals either simultaneously with the alkylating agent or up to 15 minutes before their administration.

The following amounts of the salt of the mercapto alkane sulfonic acid were necessary in order to completely avoid cystitis in all test animals:

(a) sodium salt of 2-mercapto ethane sulfonic acid: 21.5 mg./kg.
(b) sodium salt of 3-mercapto-1-propane sulfonic acid: 100 mg./kg.
(c) sodium salt of 3-mercapto-2-methyl-1-propane sulfonic acid: 100 mg./kg.
(d) sodium salt of 6-mercapto-1-hexane sulfonic acid: 100 mg./kg.

The toxicity of all of the tested salts of mercapto alkane sulfonic acids was substantially equal and very low (DL 50>2000 mg./kg.).

What I claim is:

1. Process for the treatment of humans suffering from the undesired urotoxic side effects caused by cytostatically active alkylating agents selected from the group consisting of cyclophosphamide, trofosfamide, ifosfamide, and sufosfamide in the kidneys, urinary tracts and urinary bladder comprising administering a pharmacologically acceptable salt of a mercapto alkane sulfonic acid having the general formula $$HS-alk-SO_3H,$$

wherein alk is a member selected from the group consisting of the straight and branched alkylene groups having from 2 to 6 carbon atoms, to the human treated with the alkylating agent in an amount ranging from 20% to about 100% of the weight of the dose of the alkylating agent of the salt of the mercapto alkane sulfonic acid.

2. Process as claimed in claim 1 wherein the salt of the mercapto alkane sulfonic acid is administered to the patient within the period ranging from about 30 minutes before the administration of the cytostatically active alkylating agent up to about 30 minutes after its administration.

3. Process as claimed in claim 1 wherein at least 25% of the total dose of the salt of the mercapto alkane sulfonic acid is administered in a period ranging from about 30 minutes before the administration of the cytostatically active alkylating agent until about 30 minutes after its administration while the remainder of the total dose is administered to the human in a single or in several separate partial doses within a period of up to 12 hours after the administration of the cytostatically active alkylating agent.

4. Process as claimed in claim 1 wherein the salt of the mercapto alkane sulfonic acid is administered to the human in an amount ranging from 30 to 100% of the weight of the dose of the cytostatically active alkylating agent.

5. Process as claimed in claim 1 wherein alk is the 1,2-ethylene group.

6. Process as claimed in claim 1 wherein the pharmacologically acceptable salt of the mercapto alkane sulfonic acid is an alkali metal salt.

7. Process as claimed in claim 6 wherein the pharmacologically acceptable salt is the sodium salt.

* * * * *

UNITED STATES PATENT AND TRADEMARK OFFICE

CERTIFICATE EXTENDING PATENT TERM
UNDER 35 U.S.C. 156

Patent No.    : 4,220,660

Dated         : September 2, 1980

Inventor(s)   : NORBERT BROCK

Patent Owner  : ASTA PHARMA AG

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

821 DAYS with all rights pertaining thereto as provided by 35 USC 156 (b).

I have caused the seal of the Patent and Trademark Office to be affixed this 11th day of December 1989.

Jeffrey M. Samuels
Acting Commissioner of
  Patents and Trademarks